(12) United States Patent
Norrelund

(10) Patent No.: US 9,789,078 B2
(45) Date of Patent: Oct. 17, 2017

(54) METHOD OF TOPICALLY TREATING ACTINIC KERATOSIS WITH INGENOL MEBUTATE CYCLE THERAPY

(71) Applicant: LEO Laboratories Limited, Dublin (IE)

(72) Inventor: Kirsten Norrelund, Ballerp (DK)

(73) Assignee: LEO Laboratories Limited, Dublin (IE)

(*) Notice: Subject to any disclaimer, the term of this patent is extended or adjusted under 35 U.S.C. 154(b) by 0 days.

(21) Appl. No.: 14/401,492

(22) PCT Filed: May 15, 2013

(86) PCT No.: PCT/EP2013/060024
§ 371 (c)(1),
(2) Date: Nov. 14, 2014

(87) PCT Pub. No.: WO2013/171258
PCT Pub. Date: Nov. 21, 2013

(65) Prior Publication Data
US 2015/0133542 A1     May 14, 2015

Related U.S. Application Data

(60) Provisional application No. 61/648,071, filed on May 16, 2012.

(51) Int. Cl.
*A61K 31/22* (2006.01)
*A61K 31/215* (2006.01)
*A61K 9/00* (2006.01)

(52) U.S. Cl.
CPC ............ *A61K 31/22* (2013.01); *A61K 9/0014* (2013.01); *A61K 31/215* (2013.01)

(58) Field of Classification Search
CPC .................................................... A61K 31/22
See application file for complete search history.

(56) References Cited

PUBLICATIONS

Berman, (Clin Cosmet Investig Dermatol, 2012; 5:111-112.*
International Search Report of PCT/EP2013/060024 dated Jul. 10, 2013.
Lebwohl Mark et al; "Ingenol Mebutate Gel for Actinic Keratosis", New England Journal of Medicine, vol. 366, No. 11, Mar. 15, 2012; pp. 1010-1019.
Siller Greg, et al; "PEP005 (ingenol mebutate) gel, a novel agent for the treatment of actinic keratosis: Results of a randomized, double-blind, vehicle-controlled, multicentre, phase IIa study"; Australian Journal of Dermatology, vol. 50, No. 1, Feb. 1, 2009; pp. 16-22.
Anderson Lawrence et al.; "Randomized, double-blind, double-dummy, vehicle-controlled study of ingenol mebutate gel 0.025% and 0.05% for actinic keratosis"; Journal of The American Academy of Dermatology, vol. 60, No. 6, Jun. 1, 2009; pp. 934-943.
Rosen Robert et al; "Dual mechanism of action of ingenol mebutate gel for topical treatment of actinic keratosis: Rapid lesion necrosis followed by lesion-specific immune response"; Journal of the American Academy of Dermatology; vo. 66. No. 3, Mar. 1, 2012.
Garbe et al., *Efficacy and safety of follow-up field treatment of actinic keratosis with ingenol mebutate 0.015% gel: a randomized, controlled 12-month study*, Br J Dermatol. Oct. 15, 2015. doi: 10.1111/bjd.14222. pp. 1-9.

* cited by examiner

*Primary Examiner* — Zohreh Fay
(74) *Attorney, Agent, or Firm* — Fish & Richardson P.C.

(57) ABSTRACT

The present invention relates to cyclic or repeated use of the ingenol mebutate for topical treatment of actinic keratosis lesions. Generally speaking, the present invention comprises a first ingenol mebutate treatment cycle and a second ingenol mebutate treatment cycle, wherein the first treatment cycle topically treats a treatment area with a topical gel formulated with ingenol mebutate at a selected dosage strength for a specified treatment regimen, and the second ingenol mebutate treatment cycle comprises topically re-treating the treatment area with the same topical ingenol mebutate gel for the same specified treatment regimen, if following the first treatment cycle, the treatment area failed to clear or failed to remain clear of AK lesions. The present invention further relates to spot or individual lesion therapy in the treatment area following the topical bi-cyclic therapy with ingenol mebutate.

28 Claims, No Drawings

METHOD OF TOPICALLY TREATING ACTINIC KERATOSIS WITH INGENOL MEBUTATE CYCLE THERAPY

CROSS-REFERENCE TO RELATED APPLICATIONS

This application is the national phase under 35 U.S.C. §371 of PCT International Application No. PCT/EP2013/060024, filed May 15, 2013, which claims the benefit of Provisional Patent Application No. 61/648,071, filed May 16, 2012, the entire contents of the aforementioned applications are hereby incorporated herein by reference.

FIELD OF THE INVENTION

The invention relates to a cyclic method for the treatment of actinic keratosis (AK) lesions by applying ingenol mebutate topically to the same treatment area repeatedly over a given period. Generally speaking, the present invention relates to a first ingenol mebutate treatment cycle and a second ingenol mebutate treatment cycle to treat actinic keratosis lesions in a treatment area, wherein the first treatment cycle comprises topically treating the treatment area with a topical gel formulated with ingenol mebutate at a selected dosage strength for a specified treatment regimen, and the second ingenol mebutate treatment cycle comprises topically re-treating the treatment area with the same topical ingenol mebutate gel for the same specified treatment regimen, if following the first treatment cycle, the treatment area failed to clear or failed to remain clear of AK lesions. The present invention further relates to spot or individual lesion therapy in the treatment area following the topical bi-cyclic therapy with ingenol mebutate.

BACKGROUND

Ingenol mebutate is isolated from the *Euphorbia Peplus* plant and approved by the FDA for the treatment of actinic keratosis. Actinic keratosis is a common skin condition visible as thickened, cornified, scaly lesions and characterized histologically by atypical epithelial proliferation. Actinic keratosis lesions usually develop on areas that are frequently exposed to the sun (e.g. face, ears, lips, scalp, neck, forearms, and back of the hands). The method for treating actinic keratosis as approved by the FDA consists of application of ingenol mebutate for 2-3 consecutive days on the actinic keratosis lesions as a field therapy covering 25 cm$^2$ in a single treatment cycle. AK lesions are known to recur after lesion-directed therapy and field therapy.

SUMMARY OF THE INVENTION

The present invention relates to repeated cyclic use of ingenol mebutate for treatment of AK lesions which did not disappear following the first cycle of treatment or which emerged after the first cycle of treatment, either as recurrence or developed de novo, in the previously treated area.

In one aspect of the invention, it provides a method for treating a subject with actinic keratosis in a treatment area by administration of more than one treatment cycle of ingenol mebutate.

In another aspect of the invention, it provides the method as above wherein the treatment comprises two treatment cycles.

In yet another aspect of the invention, it provides the method according to any of the aspects above wherein ingenol mebutate 0.015%, by weight, is administered topically to the treatment area.

In another aspect of the invention, it provides the method according to any of the aspects above wherein the method comprises treatment of AK lesions in a selected treatment area of up to 25 cm$^2$.

In still another of aspect the invention, it provides the method according to any of the aspects above wherein the treatment cycles are separated by at least about 8 weeks.

In another aspect of the invention, it provides at method according to any of the aspects above wherein complete clearance of the AK lesions in the selected treatment area is obtained.

In another aspect of the invention, it provides the method according to any of the aspects above wherein complete clearance of the AK lesions in the selected treatment area is obtained within about 12 months after the start of the first treatment cycle was initiated.

In yet another aspect of the invention, it provides a method according to any of the methods above for reducing the number of AK lesions in the selected treatment area.

In another aspect of the invention, it provides a method according to any of the methods above wherein local skin reactions after the second administration cycle is of about the same or less magnitude as observed after the first treatment cycle.

In another aspect the invention, it provides the method for treating AK lesions according to any of the above methods wherein the selected treatment area is located on the face or scalp of the subject.

In another aspect of the invention, it provides a method of treating actinic keratosis lesions which were not completely cleared after the start of a first treatment cycle with ingenol mebutate on a treatment area of the skin comprising applying a second treatment cycle to the same treatment area with ingenol mebutate.

In another aspect of the invention, it provides a method according to the aspect above, wherein the topical administration is with a gel formulated with about 0.015% ingenol mebutate by weight.

In an aspect of the invention provides a method according to any of the aspects above wherein the second treatment cycle comprises topically applying a gel formulated with about 0.015% ingenol mebutate by weight once daily for three consecutive days.

In another aspect of the invention, it provides a method of topically treating actinic keratosis lesions according to any of the aspects above, wherein the first treatment cycle comprises topically applying a gel formulated with about 0.015% ingenol mebutate by weight to a treatment area once daily for three consecutive days and the second treatment cycle comprises topically applying a gel formulated with about 0.015% ingenol mebutate by weight to the same treatment area once daily for three consecutive days.

In another aspect of the invention, it provides a method of treating actinic keratosis lesions according to any of the aspects above, comprising administering a second treatment cycle with topical ingenol mebutate after at least about 8 weeks following the start of administration of the first treatment cycle with topical ingenol mebutate to the same treatment area.

In another aspect of the invention, it provides a method of treating actinic keratosis lesions according to any of the aspects above, comprising administering a second treatment cycle with topical ingenol mebutate after at least about 26 weeks following the start of the administration of the first treatment cycle with topical ingenol mebutate to the same treatment area.

In another aspect of the invention, it provides a method of treating actinic keratosis lesions according to any of the aspects above, comprising administering a second treatment cycle with topical ingenol mebutate after at least about 44 weeks following the start of the administration of the first treatment with topical ingenol mebutate to the same treatment area.

In another aspect of the invention, it provides a method of treating actinic keratosis lesions according to any of the aspects above, wherein the actinic keratosis lesions are field recalcitrant or field recurrent.

In another aspect of the invention, it provides a method of treating actinic keratosis lesions according to any of the aspects above, in a selected treatment area of up to about 25 $cm^2$.

In another aspect of the invention, it provides a method according to any of the aspects above, wherein the topical application of the second treatment cycle with topical ingenol mebutate gives local skin reaction (LSRs) of about same or less magnitude as observed with topical treatment of the first treatment cycle with topical ingenol mebutate.

In another aspect of the invention, it provides a method as described in any of the aspects above, wherein the treatment area is located on face or scalp.

In another aspect of the invention, it provides a method as described in any of the aspects above wherein complete clearance of the AK lesions is defined as no clinically visible AK lesions in the selected treatment area within about 12 months after the start of the first treatment cycle with topical ingenol mebutate was initiated.

In another aspect of the invention, it provides a method according to any of the aspects above, wherein the number of AK lesions in the selected treatment area is reduced after the administration of a second treatment cycle with topical ingenol mebutate.

In another aspect of the invention, it provides a method according to any of the aspects above, wherein the AK lesions in the selected treatment area are completely cleared after the second treatment cycle with topical ingenol mebutate.

In another aspect of the invention, it provides a method for complete clearance of the AK lesions defined as no clinically visible AK lesions in the selected treatment area, about 8 weeks after the start of the second treatment cycle with topical ingenol mebutate comprising one or two treatment cycles of ingenol mebutate 0.015% applied to face or scalp in an area of up to 25 $cm^2$ wherein the two treatment cycles are separated by at least about 8 weeks.

DETAILED DISCLOSURE OF THE INVENTION

As used herein, the term "treatment area" is defined as a contiguous 25 $cm^2$ area of the skin wherein one or more AK lesions exist. In an aspect of the invention, 4 to 8 clinically typical, visible and discrete AK lesions exist in the selected treatment area. The term "selected treatment area" is also used herein. Both terms refer to the area of the skin which has been selected in a clinical study and treated according to the methods as disclosed herein.

There is a different between the clearance of an individual AK lesions and clearance of the treatment field. AK lesions that are present 8 weeks after the first treatment cycle with topical ingenol mebutate may be either AK lesions that were present at baseline and did not respond to the treatment with topical ingenol mebutate or AK lesions that developed de novo during the 8 weeks after the treatment with topical ingenol mebutate. It may be difficult or impossible to determine whether the presence of AK lesions at week 8 is due to recalcitrant AK lesions or de novo AK lesions (or both).

In the context of the present invention, "field recalcitrant" will be used to refer to AK lesions that failed to completely clear after the initial treatment with topical ingenol mebutate, whether due to recalcitrant AK lesions or de novo AK lesions.

In cases where all the AK lesions in the treated field are cleared after the first treatment cycle with topical ingenol mebutate, the later observed AK lesions may be either recurrences of previously cleared AK lesions or new AK lesions that developed within the treated field. It may be difficult or impossible to determine whether the presence of AK lesions is recurrent AK lesions or de novo AK lesions. In the context of the present invention "field recurrent" will be used to refer to AK lesions that arise in a previously cleared field or treatment area, whether due to recurrent AK lesions or de novo AK lesions.

As used herein, the term "complete clearance" of AK lesions is defined as no clinically visible AK lesions in the selected treatment area.

Treatment Regimen

In accordance with the present invention, the minimum period between the treatment cycles, i.e., the period of time between the initial treatment cycle with topical ingenol mebutate and the first possible retreatment second treatment cycle with topical ingenol mebutate is preferably at least about 8 weeks. In principle, however, the period between treatment cycles with topical ingenol mebutate may be initiated at any period time after the first treatment cycle with topical ingenol mebutate. It should be appreciated by those of skill in this art that, it was observed in the phase 3 program for FDA Picato®, that the skin in the treatment area was well-healed within about 8 weeks after the topical treatment with ingenol mebutate gel and that this was the optimal time to evaluate the efficacy of the first treatment cycle with topical ingenol mebutate. This, however, does not mean that a second treatment with topical ingenol mebutate must be started by week 8. Rather, it is contemplated by the present invention that a second treatment cycle with topical ingenol mebutate may be preferably initiated at any period at or after about week 8 following completion of the first treatment cycle with topical ingenol mebutate. In the context of the present invention, 8 weeks includes +/−5 days. In certain embodiments, the 8 weeks includes +/−4 days. In certain embodiments, the 8 weeks includes +/−3 days. In certain embodiments, the 8 weeks includes +/−2 days. In certain embodiments, the 8 weeks includes +/−1 day. In certain embodiments, the second treatment cycle with topical ingenol mebutate is a repetition of the first treatment cycle with topical ingenol mebutate.

Safety

It is believed that the repeated topical administration of ingenol mebutate on the skin in the same treatment will be safe (acceptable side effects) and effective. This belief is based upon previous clinical studies, wherein the main characteristics for the safety profile of ingenol mebutate gel includes localized application site disorders/(pruritus, pain, irritation) and local skin responses, particularly erythema, flaking, and scaling. Local adverse events following a first treatment cycle with topical ingenol mebutate are generally transient and typically resolve without sequelae within about 2 weeks of topical application of ingenol mebutate to the face or scalp and within about 4 weeks of topical application of ingenol mebutate to the trunk or extremities. It is believed that the skin responses will be about the same or possibly even less following each treatment regimen with topical ingenol mebutate, as measured by local skin response (LSR) score at day 4 after administration. The LSR Terms are as follows: Erythema, flaking/scaling, crusting, swelling, vasiculation/postulation all of which will be graded into grades 1-4. The sum of the six individual LSR scores will also be summarized to see if the local skin response is the same between each treatment cycle.

Efficacy

The invention provides a method for complete clearance of AK lesions defined as no clinically visible AK lesions in the selected treatment area, about 8 weeks after treatment of a treatment area comprising one or two treatment cycles of ingenol mebutate 0.015% applied to face or scalp in the treatment area of up to about 25 cm$^2$, wherein the two treatment cycles with the topical ingenol mebutate are separated by at least about 8 weeks.

In another aspect of the invention, it provides a method for complete clearance of AK lesions defined as no clinically visible AK lesions in the selected treatment area, 12 months after treatment with topical ingenol mebutate was initiated, comprising one or two treatment cycles of ingenol mebutate 0.015% applied to face or scalp in the same treatment area of up to about 25 cm$^2$ wherein the two treatment cycles with topical ingenol mebutate are separated by at least about 8 weeks.

In other aspect of the invention, it provides a method for reducing the number of AK lesions in a selected treatment area after treatment with topical ingenol mebutate has been initiated, wherein the treatment comprises one or two treatment cycles of ingenol mebutate 0.015% applied to face or scalp in the same treatment area of up to about 25 cm$^2$ wherein the two treatment cycles are separated by at least about 8 weeks.

Formulation

The product is administered as a topical treatment on selected treatment area on face or scalp. The product is packed individual unit-dose tubes, which are stored in a refrigerator at a temperature preferably between about 2° and about 8° C.

The active compound ingenol-mebutate is administered as a gel containing 0.015% active compound by weight formulated into a gel with isopropyl alcohol, benzyl alcohol, citric acid monohydrate, sodium citrate dihydrate. A topical gel treatment of AK lesions on body and trunk is also commercial available as a gel formulated with 0.05% ingenol mebutate, by weight, wherein the 0.05% gel is topically applied for 2 consecutive days for a first treatment cycle followed by, if necessary a second treatment cycle and/or spot or individual lesion treatment, as contemplated by the present invention.

EXAMPLES

Clinical trials will be conducted to evaluate the safety and efficacy of the use of repeated treatment use of ingenol mebutate gel as compared with a single cycle therapeutic use of topical ingenol mebutate gel on patients with multiple AK lesions on face or scalp. The methodology will be-performed as a phase 3, multi-centre randomized, stratified, double-blind, vehicle-controlled, parallel group, 12 month trial.

All subjects who qualify for this trial will have between about 4 and 8 clinically typical, visible and discrete AK lesions within a contiguous 25 cm$^2$ treatment area on the face or scalp. This area of skin will be referred to as the selected treatment area.

All subjects will be topically treated with ingenol mebutate gel, 0.015%, in the first treatment cycle. Subjects not completely cleared 8 weeks after start of treatment, or subject with AK lesions emerging in the previously cleared selected treatment area at week 26 or week 44 will be randomized 2:1 to one of the following treatments in the second treatment cycle:
  Ingenol mebutate gel, 0.015% once daily for 3 consecutive days in the selected treatment area
  Vehicle gel once daily for 3 consecutive days in the selected treatment area.

First Treatment Cycle (Day 1 to Week 8)

Subjects will sign a study specific consent form in the presence of the investigator. Once eligibility is confirmed (day 1 at visit 1.1), the selected treatment area will be marked on the skin and the subjects will topically apply the first application with ingenol mebutate gel under the supervision of the trial personnel. The second and third applications will be applied by the subject at home to complete the first treatment cycle. The next visit (day 4, visit 1.2) must be scheduled 3 days after first application with ingenol mebutate gel, at which time the selected treatment area will be assessed for local skin responses (LSRs). At 8 weeks following the first topical application with ingenol mebutate gel (day 57, visit 1.3), an assessment of the selected treatment area, including LSRs and AK lesion count, will be performed. Subjects, who are not completely cleared in the selected treatment area, will be randomized to ingenol mebutate gel or vehicle gel to start a second treatment cycle. The first unit dose of trial medication should be applied on the same day, corresponding to day 1 in the second treatment cycle. Subjects, who are completely cleared in the selected treatment area, will continue in the observation period until study completion at week 52.

Observation Period (Week 8 to Week 52)

The observation period is only applicable for subjects completely cleared at week 8. Visits will be performed at weeks 26, 44 and 52 (visits 1.4, 1.5 and 1.6 respectively) at which an assessment of the selected treatment area including LSRs and AK lesion count, will be performed. Subjects, with AK lesions emerging in the previously cleared selected treatment area at week 25 or week 44, will be randomized on the same day to ingenol mebutate gel or vehicle gel to start the second treatment cycle, corresponding to day 1 of the first treatment cycle.

Second Treatment Cycle (Period of 8 Weeks)

At day 1 in the second treatment cycle (visits 2.1, 3.1 or 4.1), the subjects will be randomized to treatment with ingenol mebutate gel or vehicle gel. The selected treatment area will be marked on the skin and the subjects will apply the first application at the site(the second and third treatment will be applied by the subjects at home). The subjects will attend visits at day 4, day 15, day 29 and day 57 after randomization, and the assessments performed will be the same as in the first treatment cycle. After completion of the second treatment cycle at 8 weeks after randomization, individual lesion treatment may be used to treat any AK lesions present or emerging in the selected treatment area. These treatments will be administered at the discretion of the investigator. Subjects receiving individual lesion treatment will continue to be followed in the trial until week 52.

Follow-Up Period(Week 16 to Week 52)

The follow-up period is only applicable for subjects who have completed the second treatment cycle (8 weeks after randomization), and the period continues until trial completion at week 52. At each visit (week 34 and week 52), an assessment of the selected treatment area, including LSRs an AK lesion count, will be performed.

A total of 454 subjects will be enrolled and have the first application with ingenol mebutate gel, 0.015% by weight, in the first treatment cycle. The percentage of scalp and face treated subjects will be controlled. Within each country, approximately 80% of subjects enrolled will be treated on the face and approximately 20% will be treated on the scalp.

It should be understood by those of skill in this art that the foregoing description and examples illustrate only certain embodiments of the present invention. The present invention therefore is not limited to the foregoing examples and illustrative embodiments and such are provided as examples only and are not intended to limit the scope of the present invention. Thus, various modifications and alterations to the present invention will become apparent to those skilled in the art without departing from the scope and spirit of this invention. That is, persons skilled in the art will appreciate and understand that modifications and variations are, or will be, possible to utilize and carry out the teachings of the present invention described herein. Accordingly, all suitable modifications, variations and equivalents may be resorted to, and such modifications, variations and equivalents are intended to fall within the scope of the present invention as described and within the scope of the claims.

The invention claimed is:

1. A method for topically treating a subject diagnosed with actinic keratosis lesions in a treatment area, said method comprising administering topically more than one treatment cycle of ingenol mebutate to the treatment area, each treatment cycle separated by an interval without treatment.

2. The method of claim 1, wherein at least two treatment cycles are administered.

3. The method according to claim 1, wherein said ingenol mebutate is administered as a topical formulation comprising ingenol mebutate 0.015%, by weight, and is applied to the face or scalp of a subject.

4. The method according to claim 1, wherein the treatment area has a size of up to about 25 $cm^2$.

5. The method according to claim 1, wherein the interval without treatment is at least 8 weeks.

6. The method according to claim 1, wherein complete clearance of actinic keratosis lesions in the treatment area is obtained.

7. The-method according to claim 1, wherein complete clearance of the actinic keratosis lesions in the treatment area is obtained as evaluated 12 months after the first treatment cycle is initiated.

8. The method according to claim 2, wherein said ingenol mebutate is administered as a topical formulation comprising ingenol mebutate 0.015%, by weight, and is applied to the face or scalp of a subject.

9. The method according to claim 2, wherein the treatment area has a size of up to about 25 $cm^2$.

10. The method according to claim 3, wherein the treatment area has a size of up to about 25 $cm^2$.

11. The method according to claim 2, wherein the two treatment cycles are separated by at least 8 weeks.

12. The method according to claim 3, wherein the treatment cycles are separated by at least 8 weeks.

13. The method according to claim 4, wherein the treatment cycles are separated by at least 8 weeks.

14. The method according to claim 2, wherein complete clearance of actinic keratosis lesions in the treatment area is obtained.

15. The method according to claim 3, wherein complete clearance of actinic keratosis lesions in the treatment area is obtained.

16. The method according to claim 4, wherein complete clearance of actinic keratosis lesions in the treatment area is obtained.

17. The method according to claim 5, wherein complete clearance of actinic keratosis lesions in the treatment area is obtained.

18. The method according to claim 2, wherein complete clearance of the actinic keratosis lesions in the treatment area is obtained as evaluated 12 months after the first treatment cycle is initiated.

19. The method according to claim 3, wherein complete clearance of the actinic keratosis lesions in the treatment area is obtained as evaluated 12 months after the first treatment cycle is initiated.

20. The method according to claim 4, wherein complete clearance of the actinic keratosis lesions in the treatment area is obtained as evaluated 12 months after the first treatment cycle is initiated.

21. The method according to claim 5, wherein complete clearance of the actinic keratosis lesions in the treatment area is obtained as evaluated 12 months after the first treatment cycle is initiated.

22. The method according to claim 6, wherein complete clearance of the actinic keratosis lesions in the treatment area is obtained as evaluated 12 months after the first treatment cycle is initiated.

23. A method for topically treating a subject diagnosed with actinic keratosis lesions in a treatment area on the face or scalp of the subject, said method comprising:
applying a topical formulation containing ingenol mebutate in an amount of 0.15% by weight to the actinic keratosis lesions in the treatment area in more than one treatment cycle to treat the actinic keratosis lesions;
wherein the treatment area has a size of up to about 25 $cm^2$; wherein each treatment cycle separated by an interval without treatment and wherein complete clearance of the actinic keratosis lesions is obtained in the treatment area.

24. A method of claim 23, wherein said method comprises a first treatment cycle and a second treatment cycle.

25. A method of claim 24, wherein the first and second treatment cycles are separated by 8 weeks.

26. A method of claim 25, wherein the complete clearance of the actinic keratosis lesions in the treatment area is obtained as evaluated at 12 months after initiation of the first treatment cycle.

27. A method of claim 1, wherein said treatment cycle includes daily topical administration of ingenol mebutate for three consecutive days.

28. A method of claim 23, wherein said treatment cycle includes daily topical administration of ingenol mebutate for three consecutive days.

\* \* \* \* \*

UNITED STATES PATENT AND TRADEMARK OFFICE
CERTIFICATE OF CORRECTION

PATENT NO. : 9,789,078 B2
APPLICATION NO. : 14/401492
DATED : October 17, 2017
INVENTOR(S) : Kirsten Noerrelund It is certified that error appears in the above-identified patent and that said Letters Patent is hereby corrected as shown below:

On the Title Page

Item (72) Inventor:
Delete "Ballerp", and insert -- Ballerup --, therefor.

In the Claims

In Column 7, Line 47, Claim 7:
Delete "The-method" and insert -- The method --, therefor.

Signed and Sealed this
Second Day of January, 2018

Joseph Matal
*Performing the Functions and Duties of the*
*Under Secretary of Commerce for Intellectual Property and*
*Director of the United States Patent and Trademark Office*